US007683050B2

(12) United States Patent
Brown

(10) Patent No.: US 7,683,050 B2
(45) Date of Patent: Mar. 23, 2010

(54) FORMULATIONS AND METHODS OF ADMINISTRATION OF CEPHALOTAXINES, INCLUDING HOMOHARRINGTONINE

(75) Inventor: Dennis M. Brown, Menlo Park, CA (US)

(73) Assignee: Chemgenex Pharmaceuticals, Inc., Menlo Park, CA (US)

( * ) Notice: Subject to any disclaimer, the term of this patent is extended or adjusted under 35 U.S.C. 154(b) by 610 days.

(21) Appl. No.: 11/497,739

(22) Filed: Aug. 1, 2006

(65) Prior Publication Data

US 2006/0269622 A1 Nov. 30, 2006

Related U.S. Application Data

(63) Continuation of application No. 10/617,927, filed on Jul. 10, 2003, now abandoned.

(60) Provisional application No. 60/396,926, filed on Jul. 17, 2002.

(51) Int. Cl.
*A61K 31/55* (2006.01)
(52) U.S. Cl. .................. 514/214.01; 514/214.03; 514/215; 424/484; 424/649; 424/725
(58) Field of Classification Search .................. None
See application file for complete search history.

(56) References Cited

U.S. PATENT DOCUMENTS

| H271 H | 5/1987 | Whaun | |
|---|---|---|---|
| 4,675,318 A | 6/1987 | Liu | |
| 4,783,454 A | 11/1988 | Liu | |
| 4,808,629 A | 2/1989 | Liu | |
| 6,395,299 B1 * | 5/2002 | Babich et al. | 424/484 |
| 6,630,173 B2 | 10/2003 | Brown | |
| 6,734,178 B2 * | 5/2004 | Brown | 514/214.01 |
| 7,169,774 B2 * | 1/2007 | Robin et al. | 514/214.01 |
| 2002/0068710 A1 * | 6/2002 | Glucksmann | 514/44 |
| 2003/0175365 A1 * | 9/2003 | Liu | 424/725 |

FOREIGN PATENT DOCUMENTS

| WO | WO 99/048894 | 9/1999 |
|---|---|---|
| WO | WO 01/68098 A2 | 9/2001 |
| WO | WO 01/68098 A3 | 9/2001 |
| WO | WO 02/032904 | 4/2004 |

OTHER PUBLICATIONS

Zhang, Wei, et al., "Enhanced production of harringtonine and homoharringtonine in *Cephalotaxus fortunei* callus culture by periodic temperature oscillation," Biotechnology Letters, vol. 20, No. 1, (Jan. 1998).
Abbott, B.J., et al., "Screening Data from the Cancer Chemotherapy National Service Center Screening Laboratories. XXXVI. Plant Extracts," Cancer Res. Supp., 26(9):1131-1136 (Sep. 1966).

Ajani, J., et al., "Phase II studies of homoharringtonine in patients with advanced malignant melanoma; sarcoma; and head and neck, breast, and colorectal carcinomas," Cancer Treat. Rep. 70(3):375-379 (Mar. 1986).
Feldman, E., et al., "Homoharringtonine is safe and effective for patients with acute myelogenous leukemia," Leukemia 6(11):1185-1188 (Nov. 1992).
Gonther, A., et al., "Differential expression of intermediate-filament proteins in murine sarcoma 180 ascites or solid tumor," Cancer Res. 44(6):2590-2594 (Jun. 1984).
Jin, X., et al., "Cisplatin combination therapy of murine S180," Shanghai Yike Daxue Xeubao, 16(1):50-54 (1989), Caplus Accession No. 1989:225174, (Abstract only).
Kantarjian, H.M., et al., "Homoharringtonine: History, Current Research, and Future Directions," Cancer 92(6):1591-1605 (Sep. 2001).
Laster, W.R., et al., "Therapeutic synergism (TS) of homoharringtonine (H) plus 5-fluorouracil (FU) against leukemia P388 (P388/0) and ARA-C-resistant P388 (P388/ARA-C)," Proc. Am. Assn. Cancer Res., 23:786 (1982), Embase Accession No. 82182588, (Abstract only).
Magnusson, K., et al., "Is conversion of solid into more anoxic ascites tumors associated with p53 inactivation?," Oncogene 17(5):2333-2337 (Nov. 1998).
Powell, R.G., "Antitumor alkaloids for *Cephalotaxus haningtonia*: structure and activity," J. Pharm. Sci. 61(8):1227-1230 (Aug. 1972).
Provencher, D., et al., "Discordance in p53 mutations when comparing ascites and solid tumors from patients with serous ovarian cancer," TumorBiol. 18(3):167-174 (1997).
Runge-Morris, M.A., et al., "Evaluation of Homoharringtonine efficacy in the treatment of sqamous cell carcinoma of the head and neck: A phase II Illinois Cancer Council Study," Invest. New Drugs 7(2-3):269-273 (Jul. 1989).
Savage, K.E., et al., "Effect of tunicamycin, an inhibitor of protein glycosylation, on division of tumour cells in vitro," J. Cell Sci. 64:295-306 (Nov. 1983).
Takano, I., et al., "Ester-type *Cephalotaxus* alkaloids from *Cephalotaxus harringtonia* var. *drupacea*," Phytochemistry, 44(4):735-738 (1997).
Takano, I., et al., "New oxygenated *Cephalotaxus* alkaloids from *Cephalotaxus harringtonia* var. *drupacea*," J. Nat. Prod. 59(12):1192-1195 (Dec. 1996).
Visani, G., et al., "Effects of homoharringtonine alone and in combination with α interferon and cytosine arabinoside on in vitro growth and induction of apoptosis in chronic myeloid leukemia and normal hematopoietic progenitors," Leukemia 11:624-628 (May 1997).

(Continued)

*Primary Examiner*—Herbert J. Lilling
(74) *Attorney, Agent, or Firm*—Morgan Lewis & Bockius LLP; Richard F. Trecartin; Tuan N. Nguyen

(57) ABSTRACT

The present invention is directed to compositions and methods for the treatment of patients with cephalotaxines, for example, homoharringtonine. The invention is also directed to improvements in the purity, manufacturing process, formulation and administration of homoharringtonine for the treatment of cancer and other aberrant cellular diseases. The invention also provides methods and compositions for antiparasitic, antifungal, antiviral and antibacterial treatments.

14 Claims, 1 Drawing Sheet

OTHER PUBLICATIONS

Warrell, R.P., et al., "Homoharringtonine: an effective new drug for remission induction in refractory nonlymphoblastic leukemia," J. Clin. Oncol. 3(5):617-621 (May 1985).

Witte, R.S., et al., "A phase II trial of amonafide, caracemide, and homoharringtonine in the treatment of patients with advanced renal cell cancer," Invest. New Drugs 14(4):409-413 (1996).

Witte, R.S., et al., "A phase II trial of homoharringtonine and caracemide in the treatment of patients with advanced large bowel cancer," Invest. New Drugs 17(3):173-177 (1999).

Yuzhu, Z., et al., "Homoharringtonine, cytarabine and aclarubicin (HAA) combination chemotherapy for acute myeloid leukemia (AML)," Chin. J. Clin. Oncol., 25(10):758-759 (1998), Embase Accession No. 1998384948, (Abstract only).

Zhang, S.D., et al., "Inhibitory effects of homoharringtonine and hydroxycamptothecin in combination with other agents on cancer cell growth," Asia Pac. J. Pharmacol., 7:191-195 (1992).

Zhou, D.C., et al., "Homoharringtonine: an effective new natural product in cancer chemotherapy," Bull. Cancer, 82(12):987-995 (Dec. 1995).

* cited by examiner

FORMULATIONS AND METHODS OF ADMINISTRATION OF CEPHALOTAXINES, INCLUDING HOMOHARRINGTONINE

This is a continuation of U.S. Ser. No. 10/617,927, filed Jul. 10, 2003, pending, which claims the benefit under 35 U.S.C. §119(e) of U.S. Ser. No. 60/396,926, filed Jul. 17, 2002, all which are hereby incorporated by reference in their entirety.

FIELD OF THE INVENTION

The present invention is directed to compositions and methods for the treatment of patients with cephalotaxines, for example, homoharringtonine. The invention is also directed to improvements in the purity, manufacturing process, formulation and administration of homoharringtonine for the treatment of cancer and other aberrant cellular diseases. The invention also provides methods and compositions for antiparasitic, antifungal, antiviral and antibacterial treatments.

BACKGROUND OF THE INVENTION

Cephalotaxanes are alkaloids extracted from skins, stems, leaves and seeds of *Cephalotaxus fortunei* Hook and other related species, such as *Cepholotaxus sinensis* Li, *C. hainanensis* and *C. wilsoniana*, including *C. oliveri* mast and *C. harringtonia*. Cephalotaxanes exhibit a unique structure, as shown in FIG. 1. Although cephalotaxine (wherein X in FIG. 1 is —OH) is abundant in *C. harringtonia*, it is devoid of biological activity. The presence of an ester side chain at C-3 appears to be critical to the antitumor potency.

Homoharringtonine (4-methyl-2-hydroxy-2-(4-hydroxy-4-methylpentyl), "HHT") is the butanediocate ester of cephalotaxine. HHT is a naturally occurring cephalotaxine compound and has the structure shown in FIG. 2.

Reports suggest that HHT can be chemically synthesized with purity greater than 99.8% and total related impurity less than 0.5% (see L. Keller, et. al., Tetrahed. Lett., 42, 1911-1913 (2001)); international publication WO 02/32904 A1). Although at least 50% of Cephalotaxus alkaloids are cephalotaxine, the use of cephalotaxine as a source for semi-synthesis of HHT has not yet been economically justified.

HHT can also be prepared from cultured cells of *C. harringtonia* (U.S. Pat. No. 4,152,214). However, unlike preparations from cultured cells, whole plant-derived HHT has been clinically tested in various cancers including a number of forms of leukemia and preleukemic conditions, such as myelodysplastic syndrome (MDS). Furthermore, HHT derived from whole plants has been widely used in China as the front-line chemotherapy for acute myeloid leukemias, particularly acute promyelocytic leukemia (APL). There is little data on efficacy and toxicity of the chemically synthesized or tissue culture derived HHT.

Also, like most anticancer agents, HHT has dose-limiting toxicities, including myelosuppression, cardiotoxicity, and hypotension. Therefore, it is highly desirable to improve the dosage form of the drug, dosage amounts, and schedule of administration. Thus, improvements are sought to improve efficacy, reduce side effects, improve quality of life and increase survival of patients.

For naturally occurring products like HHT, it is desirable to increase the purity of HHT preparations away from related analogs, as well as reduce or eliminate additives, preservatives or excipients used to make the agent more pharmaceutically acceptable. More purified preparations will reduced physiologic stresses arising from the metabolic processing of or physiological responses to unwanted impurities and undesirable excipients. For example, additives such as sodium bisulfite, used as an antioxidant in pharmaceutical preparations, are known to cause allergic or hypersensitivity reactions in some patients. This also occurs for pharmaceutical diluents such as cremophor EL. Moreover, mannitol, a pharmaceutical excipient, can cause hypotension for some patients.

The National Cancer Institute conducted clinical trials in cancer chemotherapy using a lyophilized HHT product, provided as a sterile 10-mg vial. Mannitol (50 mg) and hydrochloric acid were included in the vial. The intact vials required frozen storage (at −10° C. to −20° C.). The lyophilized HHT in vials was to be reconstituted with 4.9 mL of 0.9% Sodium Chloride Injection, USP, to obtain a solution containing HHT at 2 mg/mL and having a pH of 3 to 5. The act of reconstitution could be problematic if improperly performed.

An object of the present invention was to provide a stable, therapeutically acceptable, intravenously injectable dosage form of HHT that does not require lyophilization and reconstitution, and that can be packaged and shipped as a single vial instead of a dual-vial package.

It is another object of the present invention to provide new methods and compositions for administering HHT for periods different from current dosage forms, and to provide new administration schedules to improve efficacy and reduce side-effects associated with drug treatment.

SUMMARY OF THE INVENTION

The invention described herein encompasses a method for the manufacture of homoharringtonine in scale suitable for pharmaceutical product development.

According to another aspect of the invention, a pharmaceutical composition which comprises a therapeutically amount of HHT purified from the natural plant according to methods described herein, is provided.

According to another aspect, the invention allows for the use of HHT as a soluble liquid dosage form, stable at room temperature for over two years in a convenient form for further dilution prior to administration to patients.

In a preferred embodiment, the liquid dosage form is further diluted for intravenous administration in dosages ranging from 1 to 5 mg/m$^2$ as an infusion. Administration is intermittent or continuous for 1 to 21 days per month.

These compositions and methods are designed for improved therapeutic benefit for patients suffering with drug sensitive disease conditions, for example, cancer, for example, leukemias, preleukemia conditions or other hyperproliferative or aberrant cellular conditions.

One aspect of the invention is a process for producing homoharringtonine. The process comprises
 a) contacting a *Cephalotaxus* plant with citric acid to obtain an extraction mixture;
 b) adjusting the pH of the extraction mixture of a) to between about 8 and 9 with ammonia;
 c) extracting said extraction mixture of b) with chloroform;
 d) applying reduced pressure to the extraction mixture of c) to remove said chloroform;
 e) contacting the extraction mixture of d) with a silica gel column and eluting a purified extraction product;
 f) concentrating the purified extraction product of e);
 g) drying the concentrated purified extraction product of f);
 h) contacting the dried extraction product of g) with methanol to obtain a precipitate; and
 i) collecting said precipitate, wherein said precipitate comprises homoharringtonine.

According to one aspect of the invention, the contacting of step a) is for at least 48 hours.

According to another aspect, the adjusting of step b) is to pH 8.5.

The process of the invention may further comprise concentrating the extraction mixture of step b) under reduced pressure, contacting the concentrated extraction mixture with citric acid, extracting the concentrated extraction mixture with chloroform, and adjusting the pH of the concentrated extraction mixture to between about 5 and 8.

According to a further aspect, the contacting of step h) is at a temperature between 4° C. and 10° C. According to another aspect, the contacting of step h) is for at least 16 hours.

The homoharringtonine produced by the claimed method is at least 98% pure. According to a preferred embodiment, the homoharringtonine produced by the claimed method is at least 99% pure.

According to one aspect, homoharringtonine produced by the claimed method is dissolved in water or buffered saline without pharmaceutical excipients.

Also claimed are compositions obtained by the process of the invention. According to one aspect, the compositions do not include mannitol. According to another aspect, the compositions do not require lyophilization to create a pharmaceutically acceptable dosage form.

Also claimed herein are methods of treatment using the claimed compositions. According to one aspect, the method of treatment includes administering a composition of the invention by intravenous administration for 5 to 25 days per month. According to another aspect, the method of treatment includes administering the compositions of the invention by a non-intravenous route. According to a further aspect, the non-intravenous route is intramuscular, subcutaneous, oral or intraocular administration. The composition of the invention can alternatively be administered as a depot.

Also included in the invention are aqueous solutions of HHT. According to one aspect, an aqueous solution of HHT, which is stable, is in a unit dosage form, and is suitable for administration by injection, is covered by the present invention. The aqueous solution, in some aspects, has a concentration between 0.1 and 50 mg/mL HHT. According to other aspects, the HHT concentration is between 1 and 5 mg/mL. The aqueous solution preferably has a pH at between about 3.0 and 5.0. According to other aspects, the aqueous solution has a pH of about 4.0. The aqueous solution is, in some aspects, provided in a sealed container.

Also covered by the present invention are methods of treatment of a host with an aberrant cellular condition. The method comprises contacting a host with a cephalotaxine in an amount sufficient to modulate the aberrant cellular condition. Preferably, the contacting occurs for at least 5 consecutive days. According to one aspect, the cephalotaxine is homoharringtonine. The aberrant cellular condition, in some aspects, is cancer, leukemia, a preleukimic condition, or myelodysplastic syndrome. According to one aspect, the homoharringtonine is administered by infusion in a dose between 1 and 5 mg/m².

DETAILED DESCRIPTION OF THE FIGURES

DETAILED DESCRIPTION OF THE INVENTION

The structures of cephalotaxine analogs with various R1 and R2 substitution groups are shown in Table I, below.

TABLE I

Figure 1:
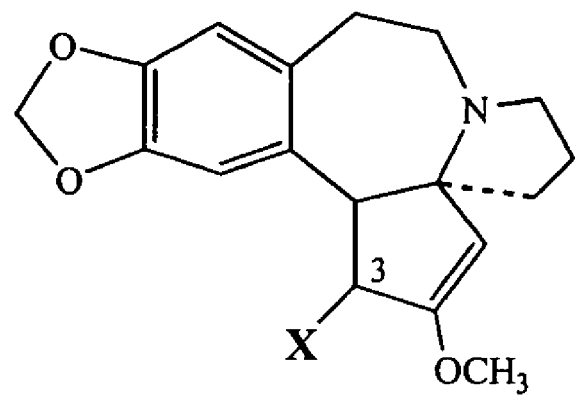
FIG. 1 depicts the general structure of a cephalotaxane. The X at position 3 is a substituent group, examples of which are shown in Table I.
Figure 2:
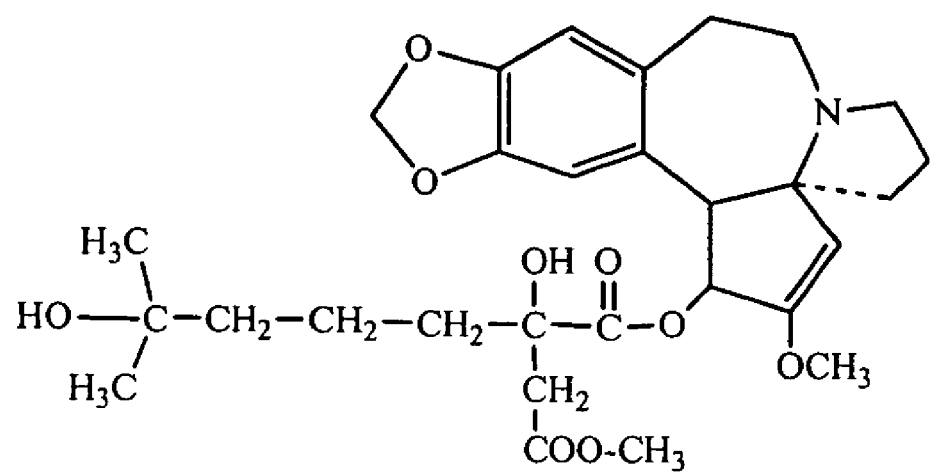
FIG. 2 depicts the structure of homoharringtonine (4-methyl-2-hydroxy-2-(4-hydroxy-4-methylpentyl), "HHT").

| X (FIG. 1) | Name |
|---|---|
| OH | Cephalotaxine |
| CH₃COO | Acetylcephalotaxine |
| (see structure) | See Table II |

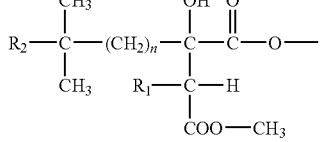

TABLE II

| R1 | R2 | n | Name |
|---|---|---|---|
| H | OH | 2 | Harringtonine (HT) |
| OH | H | 2 | Isoharringtonine (isoHT) |
| H | H | 2 | Deoxyharringtonine |
| H | OH | 3 | Homoharringtonine (HHT) |
| OH | H | 3 | Isohomoharringtonine (isoHHT) |

Preparation of HHT

Homoharringtonine (HHT) is extracted from *Cephalotaxus fortunei* Hook, f. and other related species. The process comprises extraction with citric acid or 90% ethanol, pH is then adjusted to alkaline range (pH 8.5-9.5) with ammonia or sodium carbonate. The solution is extracted with chloroform, and the chloroform is then removed under reduced pressure. The dried material is dissolved in citric acid and extracted with chloroform at gradient pH range, e.g. pH 5-7. The purified material is passed through liquid chromatography column packed with silica gel and monitored by TLC. The resulting mixture is separated by countercurrent distribution with chloroform and pH 5 buffer or tartaric acid. After removal of chloroform, the material is recrystallized from methanol. The employed process results HHT with yield about 0.002%, at least 98% pure with individual impurities less than 0.8% in concentration.

Mode of Administration

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In addition, HHT can be delivered via drug delivery devices such as cellulose acetate membranes, osmotic pump, and the like, also through target delivery system such as liposomes. The active compounds can also be administered intranasally as, for example, liquid drops or spray.

A. Oral Dosage Form

Because of their ease of administration, tablets and capsules represent a particularly advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. In preparing the oral dosage form, inactive ingredients such as starches, sugars, microcrystalline cellulose, diluents, granulating agents, lubricants, binders, disintegrating agents and the like can be used.

B. Parenteral Dosage Form

Previous HHT dosage forms have required a lyophilized preparation containing mannitol as an excipient to improve the lyophilization process, stability, reconstitution characteristics, dosage form homogeneity and solubility.

There is provided by the present invention a stable, sterile, aqueous solution of HHT in a sealed container, for example, an ampoule or vial. The solution is provided in unit dosage form suitable intravenous administration. The solution, according to one embodiment, has a concentration of HHT between about 0.1 and about 10 mg/mL. Preferably, the solution has a concentration of HHT of about 1 mg/mL. In a preferred embodiment, the solution has a pH at between 3.0 and 5.0. More preferably, the solution has a pH of about 4.0.

In a preferred embodiment, the HHT solution is free of any other added chemicals. "Free of other added chemicals" means that the solution consists of HHT as purified according to the methods of the invention, dissolved in water. In other embodiments, the HHT solution also contains a customary, physiologically acceptable excipient or carrier, for example, a preservative or buffer.

The HHT solution is preferably a stable solution. A "stable" solution is one that exhibits less than 5% loss of potency as measured by high performance liquid chromatography (HPLC) upon storage for 7 weeks at 60° C. A "stable" solution is stable at room temperature for periods of at least one year such that the active compound does not degrade by more than 5% within that time period.

In the case where an intravenous injection or infusion composition is employed, the HHT solution is provided in a suitable dosage with one or more pharmaceutically acceptable carriers, excipients or diluents. In some embodiments, the HHT solution for intravenous injection or infusion is provided in combination with one or more chemotherapeutic drugs.

The liquid dosage form may range from less than 1 mg/mL of diluent to greater than 1 mg/mL including from less than 0.1 mg/ml to soluble concentrations greater than 1 mg/ml with appropriate adjustment of pH with buffers such as tartrate, phosphate, citrate, carbonate, etc. in ranges common or standard in pharmaceutical practice.

In another embodiment, the drug dose can be introduced subcutaneously, for example, as a depot administration, where an intravenous administration is less advantageous. In one embodiment, a depot administration is utilized in concentrations where drug particles are employed to dissolve slowly for sustained drug release.

A liquid dosage form, a buffered water soluble form without pharmaceutical excipients such as mannitol are infused over a duration of days preferably between 5 and 25 days per month more preferably between 7 and 21 days utilizing dosages between 1 and 5 mg/m$^2$, preferably between about 2 and 4 mg/m$^2$. In a preferred embodiment, anti-proliferative effects are achieved in patients suffering from cancer, including leukemia including acute promyelocytic leukemia (APL), acute myeloid leukemia (AML) and chronic myeloid leukemia (CML) and preleukemia conditions including myelodysplastic syndrome or patients with other hyperproliferative aberrant cellular conditions through administration of HHT produced as a liquid dosage form, stable at room temperature of at least 98% purity dissolved in buffered water or saline without excipients such as mannitol administered by infusion to patient for a duration of 5 days or greater. In addition the dosage form can be administered with other chemotherapeutics such as antineoplastics including Gleevec, interferon, retinoic acids and the like.

The agents are provided in amounts sufficient to modulate aberrant cellular conditions such as solid cancers, leukemias, pre-leukemia conditions such as myelodysplastic syndrome, lymphomas and other aberrant hyperproliferative conditions. In one embodiment, modulation of an aberrant cellular condition comprises a reduction in tumor cell number or growth. In another embodiment, modulation of an aberrant cellular condition comprises inhibition of cell division and tumor cell growth. In other embodiments, modulation of an aberrant cellular condition comprises cytostasis. In still other embodiments, specific dosages, blood concentrations are delivered to the patient to affect cellular targets or enzymes unique to the actions of the compounds such as enzymes like telomerase, histone deacetylase or cellular targets such as histones, G protein coupled receptors and the like.

In some embodiments of the invention, modulation of an aberrant cellular condition comprises cytostasis or cytotoxicity. "Cytostasis" is the inhibition of cells from growing, while "cytotoxicity" is defined as the killing of cells.

In a preferred embodiment, a therapeutically effective dose of the compositions of the invention are administered to a patient in need of treatment. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals. Thus, the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, successful administration of composition of the invention prior to onset of the disease results in "treatment" of the disease. As another example, successful administration of HHT after clinical manifestation of the disease to combat the symptoms of the disease comprises "treatment" of the disease. "Treatment" also encompasses administration of HHT after the appearance of the disease in order to eradicate the disease. Successful administration of an agent after onset and after clinical symptoms has been developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

EXAMPLES

The following examples, given without implied limitation, show how the invention can be put into practice.

Example 1

Commercial Scale Manufacturing of HHT 90 kg of the pieces of *Cephalotaxus fortunei* Hook, f. and 70 L of tap water are added in a cloth bag and soaked twice with 500 L citric acid for 48 hours followed by 500 L tap water. pH of the soak solution is adjusted to 8.5 with ammonia and then extracted with columns containing chloroform at 300 mL/min. The chloroform solution is concentrated under reduced pressure. Three of the concentrated solutions are combined and dried. Dried material is dissolved in 800 L chloroform and extracted with 2.5 L citric acid. The acid extraction solutions are combined and extracted with chloroform at pH 5, 6, 7 and 8, adjusted with ammonia. Chloroform is removed under vacuum and dried material is dissolved in chloroform and extracted with silica gel column monitored by thin-layer chromatography. The portions containing HHT is dried, then dissolved in 5 times volume of chloroform and extracted 4 times with tartaric acid. After removal of chloroform, the dried material is dissolved in methanol and precipitated at 4-10° C. for about 16 hours. The methanol/water mixture (1:2) is filtered, rinsed and dried. The crystallization step is repeated until the color is changed from dark reddish brown to canary. Then, the crystal is crystallized in methanol and discolored with activated carbon. The recrystallization step is repeated several times until the color changed to off-white. The purified material is dried under vacuum at 40-60° C. for 7 days.

The process if the invention can produce the homoharringtonine with a typical yield of about 0.05 g homoharringtonine per kg of *Cephalotaxus fortunei* Hook, f., and with a purity of greater than 99%.

Example 2

Manufacture of Aqueous, Stable, Sterile HHT with Tartaric Acid

1. Dissolve tartaric acid in 80% batch quantity of Water for Injection.
2. Dissolve homoharringtonine and dilute to final volume to yield a final concentration of tartaric acid at 0.4 mg/mL and homoharringtonine at 1 mg/mL.
3. Adjust pH to 4.0 with NaOH and/or HCi, if necessary.
4. Filter the solution through a 0.22-μm filter.
5. Fill the filtered solution into the pre-sterilized containers (vials or ampoules) under aseptic conditions and seal.
6. Terminally sterilize the filled ampoules at 121° C. for at least 15 minutes.

Example 3

Manufacture of Aqueous, Stable, Sterile HHT without Tartaric Acid

1. Dissolve homoharringtonine in about 80% batch quantity of Water for Injection.
2. Adjust pH to 4.0 with NaOH and/or HCl.
3. Filter the solution through a 0.22-μm filter.
4. Fill the filtered solution into the pre-sterilized containers (vials or ampoules) under aseptic conditions and seal.
5. Terminally sterilize the filled ampoules at 121° C. for at least 15 minutes.

Advantages of liquid product over lyophilized product:
1. Liquid form is less expensive. Lyophilization is an expensive manufacturing process (equipment, time, energy, etc.).
2. Liquid form requires less packaging. Lyophilized product requires dual vial packaging, containing lyophilized vial and diluent vial, extra manufacturing, packaging and labeling costs, and extra room for storage, shipping.
3. Liquid form preparation involves less time, expense, waste and risk. More preparation steps are required for a lyophilized product, more hazardous waste is generated, and risks associated with contamination and safety are increased.
4. Liquid form is safer. Improper reconstitution can lead to an inaccurate dose.

Example 4

Method of High-Performance Liquid Chromatography

HHT is chromatographed on a reverse-phase isocratic HPLC system employing a mobile phase consisting of 24% of acetonitrile and 76% acetic acid (pH adjusted to 6.5 with 0.5% triethyleneamine) with a Keystone BDS Hypersil 5-μm C18 column. Detection is achieved by monitoring the UV absorbance at 288 nm and quantification is accomplished by peak area measurement with external calibration. Specificity, linearity, precision and accuracy have been demonstrated.

This method is applicable to bulk powder and liquid dosage formulations.

Example 5

Administration of Aqueous, Stable, Sterile HHT

The liquid or lyophilized dosage forms can be administered by intravenous infusion by adding the drug product in diluent including, but not limited to, Sterile Water for Injection, Bacteriostatic Water for Injection, Dextrose (2.5%, 5%, 10%), Dextrose-saline combination, Fructose (10%), Fructose in saline, Ringer's Injection, Lactated Ringer's Injection, Sodium Chloride (0.45%, 0.9%) or combination with one or more additional drugs.

Possible Process Steps to Improve Yield and Purity
Employing the following steps may improve the yield.
1. Extract at optimal pH range (e.g. 5-7) in step 6.
2. Use other acid solution (e.g. hydrochloric acid, acetic acid) in step 8 to replace tartaric acid.
3. Use methanol instead of methanol/water mixture in step 11 for purification.
4. Use specific part of tree (e.g. leaves, root, etc.) containing enriched content of homoharringtonine from *Cephalotaxus fortunei* Hook, f.

The purity of the final product can be improved by the following steps.
1. Extract with different solvent (e.g. acetone, ether, etc.) to remove impurity found in the HPLC chromatography with relative retention time of 1.1 minutes.
2. Use gradient column chromatography in step 7.

3. Combine more pure portions in steps 5 and 7 monitored by thin-layer chromatography.

I claim:

1. A sealed container consisting essentially of an aqueous solution of homoharringtonine (4-methyl-2-hydroxy-2-(4-hydroxy-4-methylpentyl) (HHT), wherein said solution is free of pharmaceutical excipients and said sealed container is an ampoule or a vial.

2. A sealed container according to claim 1, wherein said HHT is in a dosage form.

3. A sealed container according to claim 1, wherein said HHT is a citrate salt of HHT.

4. A sealed container according to claim 1, wherein said HHT is a tartrate salt of HHT.

5. A sealed container according to claim 2, wherein said dosage form is suitable for oral administration.

6. A sealed container according to claim 5, wherein said HHT is present in said oral dosage form at about 0.1%.

7. A sealed container according to claim 5, wherein said HHT is present in said oral dosage form at about 2% to about 60%.

8. A sealed container according to claim 2, wherein said dosage form is suitable for subcutaneous administration.

9. A sealed container according to claim 8, wherein said subcutaneous dosage form is a subcutaneous depot.

10. A sealed container according to claim 9, wherein said subcutaneous depot contains HHT particles.

11. A sealed container according to claim 9 or 10, wherein said depot provides slow and sustained release of said HHT.

12. A sealed container according to claim 2, wherein said dosage form is suitable for intramuscular administration.

13. A sealed container according to claim 2, wherein said dosage form is suitable for topical administration.

14. A sealed container consisting essentially of an aqueous solution of homoharringtonine (4-methyl-2-hydroxy-2-(4-hydroxy-4-methylpentyl) (HHT) in a dosage form free of pharmaceutical excipients, wherein said HHT is a tartrate salt of HHT and said sealed container is an ampoule or a vial.

* * * * *